US007895054B2

(12) United States Patent
Slen et al.

(10) Patent No.: US 7,895,054 B2
(45) Date of Patent: Feb. 22, 2011

(54) PHARMACY PERSONAL CARE ACCOUNT

(75) Inventors: Benjamin E. Slen, Louisville, KY (US); Cullen L. Reed, Louisville, KY (US); Elizabeth D. Bierbower, Wellesley, MA (US); Maureen M. Kinser, Louisville, KY (US); Jonathan T. Lord, Louisville, KY (US); Sandra L. Bartel, Green Bay, WI (US)

(73) Assignee: Humana Inc., Louisville, KY (US)

( * ) Notice: Subject to any disclaimer, the term of this patent is extended or adjusted under 35 U.S.C. 154(b) by 1448 days.

(21) Appl. No.: 11/197,200

(22) Filed: Aug. 4, 2005

(65) Prior Publication Data
US 2005/0267784 A1 Dec. 1, 2005

Related U.S. Application Data

(63) Continuation-in-part of application No. 11/119,125, filed on Apr. 29, 2005.

(60) Provisional application No. 60/568,517, filed on May 6, 2004, provisional application No. 60/572,586, filed on May 19, 2004, provisional application No. 60/601,918, filed on Aug. 16, 2004.

(51) Int. Cl.
*G06Q 10/00* (2006.01)
*G06Q 50/00* (2006.01)
*G06Q 40/00* (2006.01)
*A61B 5/00* (2006.01)
*G06F 19/00* (2006.01)

(52) U.S. Cl. .................................. 705/2; 705/3; 705/4

(58) Field of Classification Search .................. 705/2–3
See application file for complete search history.

(56) References Cited

U.S. PATENT DOCUMENTS 4,648,037 A 3/1987 Valentino (Continued)

FOREIGN PATENT DOCUMENTS

EP 1345147 9/2003

OTHER PUBLICATIONS

Toran, Mindy W., "Employers weigh their options: With health care costs rising out of control and increasing consumer dissatisfaction with managed care, employers have begun looking at new options for delivering health care benefits." Risk and Insurance, Apr. 1, 2002.*

(Continued)

*Primary Examiner*—Robert W Morgan
*Assistant Examiner*—Eliza Squires
(74) *Attorney, Agent, or Firm*—Standley Law Group LLP

(57) ABSTRACT

A method for providing insurance coverage to a subscriber comprises offering an insurance policy to said subscriber wherein said insurance policy comprises providing allowances to pay for one or more expenses covered by said insurance policy and providing monetary credits to said subscriber for any unused portion of a given allowance where said monetary credits can be used to cover the cost of a subsequent allowed expense. The insurance policy may be a pharmacy benefits plan. The covered expenses may be pharmacy expenses. The allowed expenses may be medical expenses which qualify under section 213 of the US Internal Revenue code for payment by an employer without said subscriber having to declare said payment as taxable income.

14 Claims, 3 Drawing Sheets

U.S. PATENT DOCUMENTS

| | | | |
|---|---|---|---|
| 7,660,755 B2 * | 2/2010 | Amato et al. | 705/34 |
| 2001/0037216 A1 | 11/2001 | Oscar et al. | |
| 2002/0087444 A1 | 7/2002 | DiPiero et al. | |
| 2002/0111832 A1 | 8/2002 | Judge | |
| 2002/0128879 A1 | 9/2002 | Spears | |
| 2002/0133375 A1 | 9/2002 | Moore et al. | |
| 2002/0147617 A1 | 10/2002 | Schoenbaum et al. | |
| 2002/0188480 A1 | 12/2002 | Liebeskind et al. | |
| 2003/0120515 A1 | 6/2003 | Geller | |
| 2003/0154104 A1 | 8/2003 | Koningsberg | |
| 2004/0039599 A1 | 2/2004 | Fralic | |
| 2004/0083123 A1 | 4/2004 | Kim et al. | |
| 2004/0103002 A1 | 5/2004 | Colley et al. | |
| 2004/0117323 A1 | 6/2004 | Mindala | |
| 2005/0010446 A1 | 1/2005 | Lash et al. | |

OTHER PUBLICATIONS

Gordon, Jennifer, "Humana associates testing new prescription program" Jul. 11, 2003 Business First.*

Meyer, Ann, "Health-care plan eases hit of high deductibles", Apr. 21, 2003 Chicago Tribune.*

Cvach et al., "Taxation of Compensation and Benefits" Sep. 2002 Corporate Business Taxation Monthly.*

Danzon, Patricia M., Reference Pricing: Theory and Evidence, Research Paper for the Study of Reference Pricing from Wyeth Ayerst, May 22, 2001, 38 pages, The Wharton School, University of Pennsylvania.

Humana Inc., Goals & Concepts of Drug Bucket Team, PowerPoint Presentation, Spring 2002.

Humana Inc., Goals and Concepts of Rx2004—Drug Buckets, PowerPoint Presentation, Jun. 2002.

Warren, Betsy, Humana's Strategy for Addressing Pharmacy Industry Trends, Oct. 3, 2001 8 pages.

Jacob, Julie A., Humana's Drug Benefit Linked to Cost Trade-Offs, AMNews, Jun. 3, 2001, 2 pages.

Gordon, Jennifer, Pricing it right, Business First, Apr. 19, 2002, 2 pages.

Paying the price—Some insurers base drug payments on drug cost, Star Banner, Mar. 20, 2004, 3 pages, http://www.starbanner.com/apps/pbcs.dll/article?AID+/20040320/NEWS/203200318/1009/BUSI...

Fendrick, A. Mark, et al., A Benefit-Based Copay for Prescription Drugs: Patient Contribution Based on Total Benefits, Not Drug Acquisition Cost, The American Journal of Managed Care, Sep. 2001, pp. 861-867, vol. 7 No. 9.

Wechsler, Jill, Humana revises pharmacy benefits, Newswire, Managed Healthcare Executive, Jun. 2001, pp. 7-8, 10.

Pallarito, Karen, HMO rolls out new drug benefit design, Factiva, Reuters Health E-Line, Jul. 8, 2003, 2 pages from website, http://global.factiva.com/en/arch/save_results.asp.

Humana Launches Revolutionary Prescription Drug Coverage in Ongoing Effort to Expand Choice and Control . . ., Factiva, PR Newswire, Jul. 2, 2003, 2 pages from website, http://global.factiva.com/en/arch/sav_resuls.asp.

Humana's consumer-driving pharmacy plan not dependent on drug trend, rebates, LookSmart's Find Articles, Jul. 25, 2003, 3 pages from website, http://www.findarticles.com/p/articles/mi_m0NKV/is_8_4/ai_106060093/print.

HumanaPPO Rx4 Prescription Drug Coverage brochure, Apr. 2002, 2 pages.

Humana Inc.'s RxImpact (RxAllowance) Drug List, Apr. 1, 2004, 3 pages.

Humana Inc.'s RxImpact (RxAllowance) Drug List, Mar. 1, 2004, 3 pages.

Humana Inc.'s RxIpact Drug List, Apr. 2005, 6 pages.

CMS (Centers for Medicare & Medicaid Services), Medicare Marketing Guidelines For: Medicare Advantage Plans (MAs), Medicare Advantage Prescription Drug Plans (MA-PDs), Prescription Drug Plans (PDPs) and 1876 Cost Plans, Published Aug. 15, 2005, Revised Nov. 1, 2005, 2nd Revision: Jul. 25, 2006, 36 pages.

Gordon, Jennifer, Humana associates testing new prescription program, Business First, Jul. 11, 2003, 1 page.

Chao, Schumarry, Mass Customization—The Next Generation of Pharmacy Management, Decision Maker News in Managed Care, 2003, pp. 5-7.

Humana Inc., Here's your NEW member ID and HumanaAccess Visa card—all in one!, brochure, Apr. 2004, 4 pages.

Humana Plan Descriptions, 2003, 2 pages from website.

* cited by examiner

PHARMACY PERSONAL CARE ACCOUNT

CROSS-REFERENCE TO RELATED APPLICATION

This application is a continuation-in-part and claims the benefit of the filing date of U.S. nonprovisional patent application Ser. No. 11/119,125 filed Apr. 29, 2005, entitled "Pharmacy Benefits Design", and with inventors Elizabeth M. Warren et al. Said nonprovisional application is incorporated herein by reference.

Said nonprovisional application entitled "Pharmacy Benefits Design", in turn, claims the benefit of the filing date of U.S. provisional patent application Ser. No. 60/568,517, filed May 6, 2004, and entitled "Pharmacy Benefits Design". Said provisional application is incorporated herein by reference.

Said nonprovisional application entitled "Pharmacy Benefits Design" also claims the benefit of the filing date of U.S. provisional patent application Ser. No. 60/572,586, filed May 19, 2004, and entitled "Pharmacy Benefits Calculator". Said provisional application is incorporated herein by reference.

Said nonprovisional application entitled "Pharmacy Benefits Design" also claims the benefit of the filing date of U.S. provisional patent application Ser. No. 60/601,918, filed Aug. 16, 2004, and entitled "Pharmacy personal care account". The instant application also directly claims the benefit of the filing date of said U.S. provisional patent application Ser. No. 60/601,918. Said provisional application is incorporated herein by reference.

FIELD OF THE INVENTION

The invention is in the field of insurance.

BACKGROUND

There is a long felt need in the health care industry to provide an employer sponsored health insurance policy that simultaneously covers the majority of an employee's health care costs while at the same time encourages cost savings behavior by said employee.

Co-pending U.S. patent application "Pharmacy Benefits Design", U.S. application Ser. No. 11/119,125 filed Apr. 29, 2005, for example, describes a system and method for providing health insurance to an employee (i.e. an "insured" or a "subscriber") wherein said health insurance comprises a pharmacy benefits plan and wherein said pharmacy benefits plan provides a monetary allowance for each prescription of drugs that said insured purchases. If the insured purchases a drug, the insured only has to pay for the cost of the drug that is in excess of the allowance up to a per script maximum. Said plan is referred to herein as an RxImpact plan.

All drugs within an RxImpact plan are categorized into one of four or five Groups. The Groups are A, B, C, D and optionally E. All drugs within the same group have the same allowance per prescription.

Each group contains all drugs that have a similar effect on anticipated future medical costs that an insured would face if they did not take the drugs in a timely manner. Drugs are assigned to Group A, for example, if it is anticipated that not taking them would result in significant future medical costs for an insured within one year. Antibiotics, for example, would be categorized as Group A drugs. If an insured did not take an antibiotic when prescribed, then it is anticipated that said insured would likely require future medical treatment, such as an emergency room visit or a hospitalization.

Group B drugs might comprise those that would result in significant medical costs which are incurred in a time frame that exceeds one year. Anti-cholesterol drugs are an example of Group B drugs. If an individual fails to take his/her anti-cholesterol medication in the short term, that individual may have a heart attack requiring hospitalization sometime in the future.

Group C drugs might comprise those that would not result in future medical costs if not taken, but might result in increased employee productivity. Non-sedating antihistamines are examples of Group C drugs.

Group D drugs might comprise those that would not result in either subsequent health care costs or reduced employee productivity if not taken, but might improve an insured's lifestyle. Hair restoration drugs are examples of Group D drugs.

Optional Group E drugs might comprise those that do not fall into one of the above four Groups. Anesthesia drugs are examples of Group E drugs.

Under an RxImpact pharmacy benefits plan, both generic and brand name drugs that are prescribed for the same indication would be assigned to the same Group. Lipitor (brand name) and Lovastatin (generic) are both prescribed for the treatment of high cholesterol and would therefore be assigned to the same Group, Group B. They would also, therefore, have the same allowance.

Furthermore, drugs prescribed for different indications might also be assigned to the same Group provided they had similar impact on subsequent medical costs. Antibiotics and diabetes drugs, for example, are prescribed for very different indications. Antibiotics are prescribed to treat infections. Diabetes drugs are prescribed to control blood sugar. Yet both antibiotics and diabetes drugs would be assigned to Group A since it is anticipated that not taking either of them would result in subsequent higher medical costs, such as an emergency room visit, within a year.

Different Groups of drugs in an RxImpact plan might have different allowances per prescription. Group A drugs, for example, might get an allowance of $30 for each prescription. Group B drugs might have an allowance of $20 per prescription. Group C drugs might have an allowance of $10 per prescription. Groups D and E might not have an allowance.

Group D drugs might not have an allowance since an employer offering an RxImpact plan to their employees might not wish to provide health care coverage for drugs that are primarily prescribed to enhance a person's lifestyle but do not result in the reduction of subsequent health care costs or increased employee productivity.

Group E drugs might not have an allowance since they are not covered by the RxImpact Plan.

Often times the cost of a given prescription is less than the allowance for said prescription. It has been discovered that the concept of an RxImpact plan would be more acceptable to employees and employees might be more savvy shoppers if a means could be provided whereby said employees could accumulate monetary credits for any unused portion of a given allowance provided for a given pharmaceutical purchase. An RxImpact plan would also be more acceptable if said monetary credits could be accumulated by employees without said employees having to declare said monetary credits as taxable income. An RxImpact plan would also be more acceptable if a convenient means could be provided to inform employees of the accumulation of their monetary credits. An RxImpact plan would also be more acceptable if a convenient means could be provided for employees to redeem their monetary credits for other health care costs beyond merely pharmaceutical costs.

SUMMARY OF THE INVENTION

The Summary of the Invention is provided as a guide to understanding the invention. It does not necessarily describe the most generic embodiment of the invention or all species of the invention disclosed herein.

The present invention is a method and apparatus for providing insurance coverage to a subscriber. The method comprises offering an insurance policy to said subscriber. The insurance policy provides allowances to pay for certain covered expenses. If the actual cost of a covered expense is less than the allowance for that expense, then a monetary credit is applied to a personal care account for the subscriber. The subscriber may then use the monetary credit to offset or pay for the subscriber's cost share (e.g., deductible, copay) for certain other products or services covered under the policy. These other products or services are referred to herein as "allowed expenses". The allowed expenses may or may not be the same as the covered expenses.

The method further comprises the insurance company accepting payment of a premium so that the insurance coverage will be in force. The premium may be paid in part by the subscriber and in part by another entity, such as the employer of the subscriber.

Alternatively, an employer may serve as said insurance company in the sense that said employer directly pays the benefits of said insurance coverage. This is known as a "self funded" insurance program. Said employer then, in essence, pays premiums to itself. Said premiums being equal to the cost of providing said benefits.

An employer that serves as an insurance company many, in turn, may hire a licensed insurance company, such as Humana Inc. of Louisville Ky., to administer their insurance coverage. The employer would then pay the licensed insurance company an administration fee.

The offering of a policy and the acceptance of a premium may be carried out at least in part by one or more information systems. For example, the policy may be offered via the Internet. Acceptance of the premium may be by acceptance of an electronic funds transfer.

The insurance policy may be a health insurance policy comprising a pharmacy benefits program. The invention, however, is not limited to health insurance policies or pharmacy benefits programs.

An example of a suitable pharmacy benefits program is an RxImpact plan.

The present invention is useful for increasing the acceptance among potential subscribers of a pharmacy benefits program wherein a single allowance is provided for each purchase of a prescription drug, said drug belonging to a given set of drugs. A given set of drugs, for example, may be those drugs that provide for a reduction of subsequent health care costs within a year. Each drug within the given set of drugs would have the same allowance irrespective of whether or not said drug was a generic or brand name drug.

The present invention is further useful in encouraging subscribers to request low cost but nonetheless effective pharmaceutical alternatives to treat a given indication. This lowers the overall cost of providing the pharmaceutical benefits program.

The present invention may comprise a debit card. The debit card is used by a subscriber to pay for allowed expenses using the credits from covered expenses.

DETAILED DESCRIPTION

Figure 1:
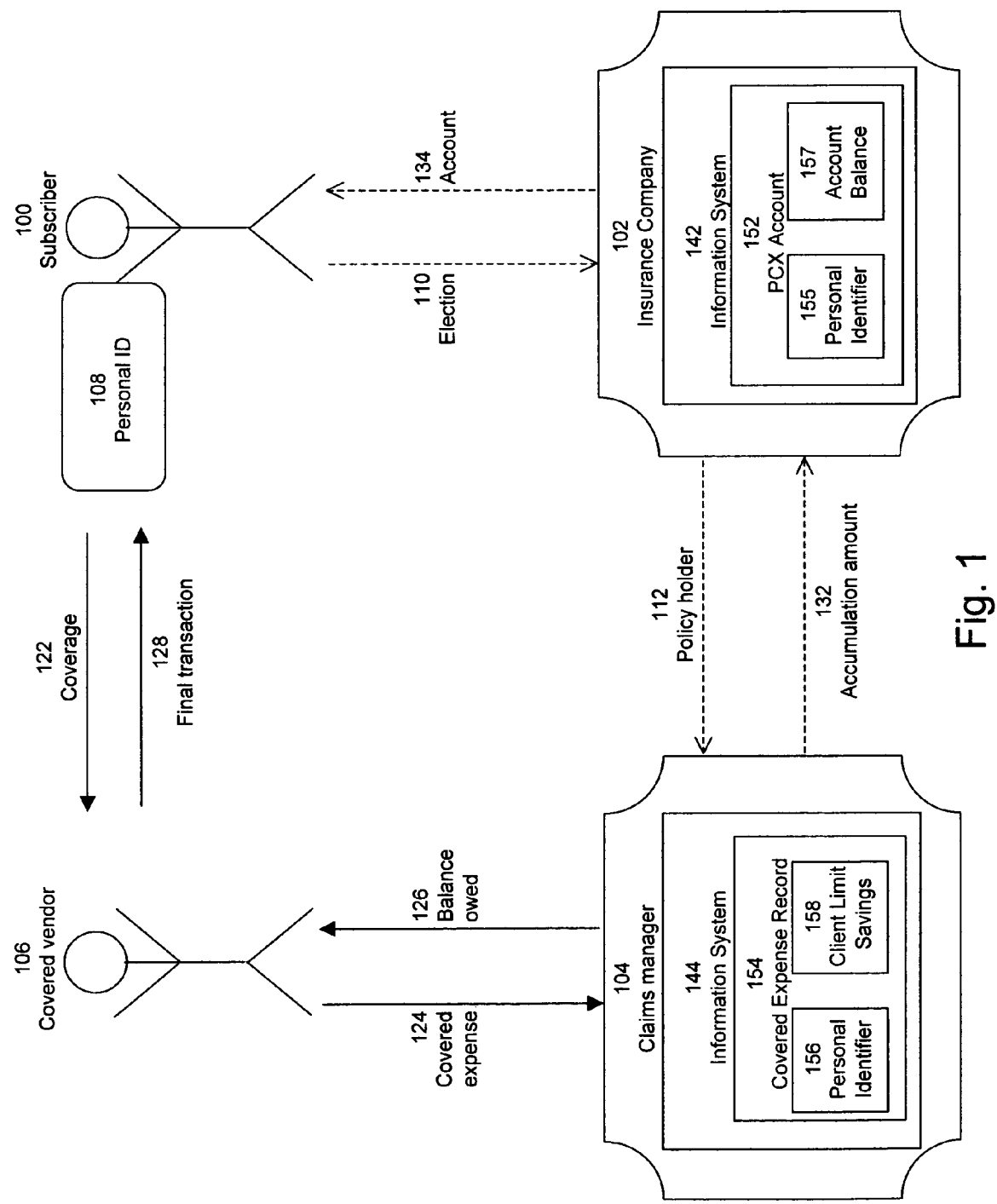
FIG. 1 is a diagram of the flow of information that occurs when a subscriber purchases a covered expense.

The following detailed description discloses various embodiments and features of the invention. These embodiments and features are meant to be exemplary and not limiting.

Definitions

The definitions provided below are to be applied to their respective terms or phrases as used herein unless the context of a given particular use of a given term or phrase clearly indicates otherwise.

The terms "health insurance", "health care plan", or "benefit plan" refer to an insurance plan that pays benefits to an insured in the event that said insured incurs covered medical costs.

The term "pharmacy benefits plan" or the like refers to an insurance plan that provides benefits to an insured for certain prescription and other drug costs. A pharmacy benefits plan may be a subset of a given health insurance plan. A pharmacy benefits plan may also be a stand-alone insurance policy.

The term "plan year" refers to an annual period for which a given health care plan is in force.

The term "open enrollment period" refers to a period of time that a prospective insured can select their health care plan for an upcoming plan year.

The term "insured" or "subscriber" refers to one or more persons who purchase and/or are covered by an insurance policy, such as a health insurance policy. A subscriber may be an employee of an employer who provides medical insurance to their employees. A subscriber may also be a dependent, spouse, partner, or other family member of said employee.

The term "prospective insured" refers to a person who is considering enrolling in a given insurance plan.

The term "benefit" or the like refers to money or other consideration provided by an insurance company to an insured as compensation for a covered event.

The phrase "out-of-pocket costs", the abbreviation "OOP", or the like refer to the portion of an insurance claim that an insured must pay directly.

The term "Health Plan Wizard" refers to one or more web pages or the like that a prospective insured would use to enroll in a given health insurance plan.

The term "cost" refers to the sale price of a particular item in question, such as a pharmacy script.

The terms "script", "prescription", "pharmacy script" and the like refer to an order for a given quantity of a given drug.

The term "information system" or the like refers to one or more of computers, servers, input devices, output devices, data storage devices, telecommunications equipment and software. Information systems may communicate with other information systems via telecommunications means, such as the Internet. Information systems may also communicate with persons via input/output devices. Persons may communicate with other persons using information systems.

Monetary quantities disclosed herein are in US dollars as of August 2005. Said quantities may be converted to other currencies at other times using published exchange rates and appropriate inflation factors.

The terms "Group", "level" or "tier" refer to a category assigned to a given script under a given pharmacy benefits plan. Said category is used to determine the coverage of a given script under said given pharmacy benefits plan. "Groups" are generally used with respect an RxImpact plan or other plan based on allowances for a given script. "Level" or "tier" are generally used with respect to a copay plan.

The phrase "covered expense" refers to an expense that is reimbursable at least in part by an insurance policy. A covered expense may be a good or service.

The phrase "allowed expense" refers to an expense that is payable from a personal care account or the like under the terms of an insurance policy. An allowed expense may be a good or service.

The phrase "personal care account" or "PCX" refers to an account that is maintained on behalf of a subscriber which contains monetary credits which can be used by the subscriber to pay for allowed expenses.

A personal care account may also be a Health Reimbursement Arrangement as defined by Section 105 of the United States Internal Revenue Code as of June 2004. Said Section 105 is incorporated herein by reference.

A "monetary credit" is a credit that is denominated in currency or one that can be converted to a denomination of currency.

Information Flow when Purchasing a Covered Expense

FIG. 1 illustrates the flow of information of the present invention when a subscriber purchases a covered expense. The figure shows subscriber 100, insurance company 102, claims manager 104, and covered vendor 106. The subscriber has personal ID card 108.

The subscriber and covered vendor are shown as stick figures.

The insurance company and claims manager are shown as rectangles with recurved corners.

The insurance company comprises an information system 142 and employees (not shown). The information system comprises computers, software, input/output devices and communications devices.

The claims manager comprises an information system 144 and employees (not shown). The information system comprises computers, software, input/output devices and communications devices.

Information that is transferred in real time is shown as solid head arrows (e.g. arrow 122). Real time information transfer implies that the information is transferred during a particular transaction and generally occurs on a time scale of minutes, seconds or less.

Information that is transferred in batches (e.g. arrow 110) is shown as open head, dashed arrows. Batch information transfer implies that comparable information for a plurality of persons or entities is transferred at once. Batch information transfer is commonly done at hourly, daily, monthly or yearly intervals. The interval chosen is that which is appropriate to the needs of those sending or receiving the information.

Figure 2:
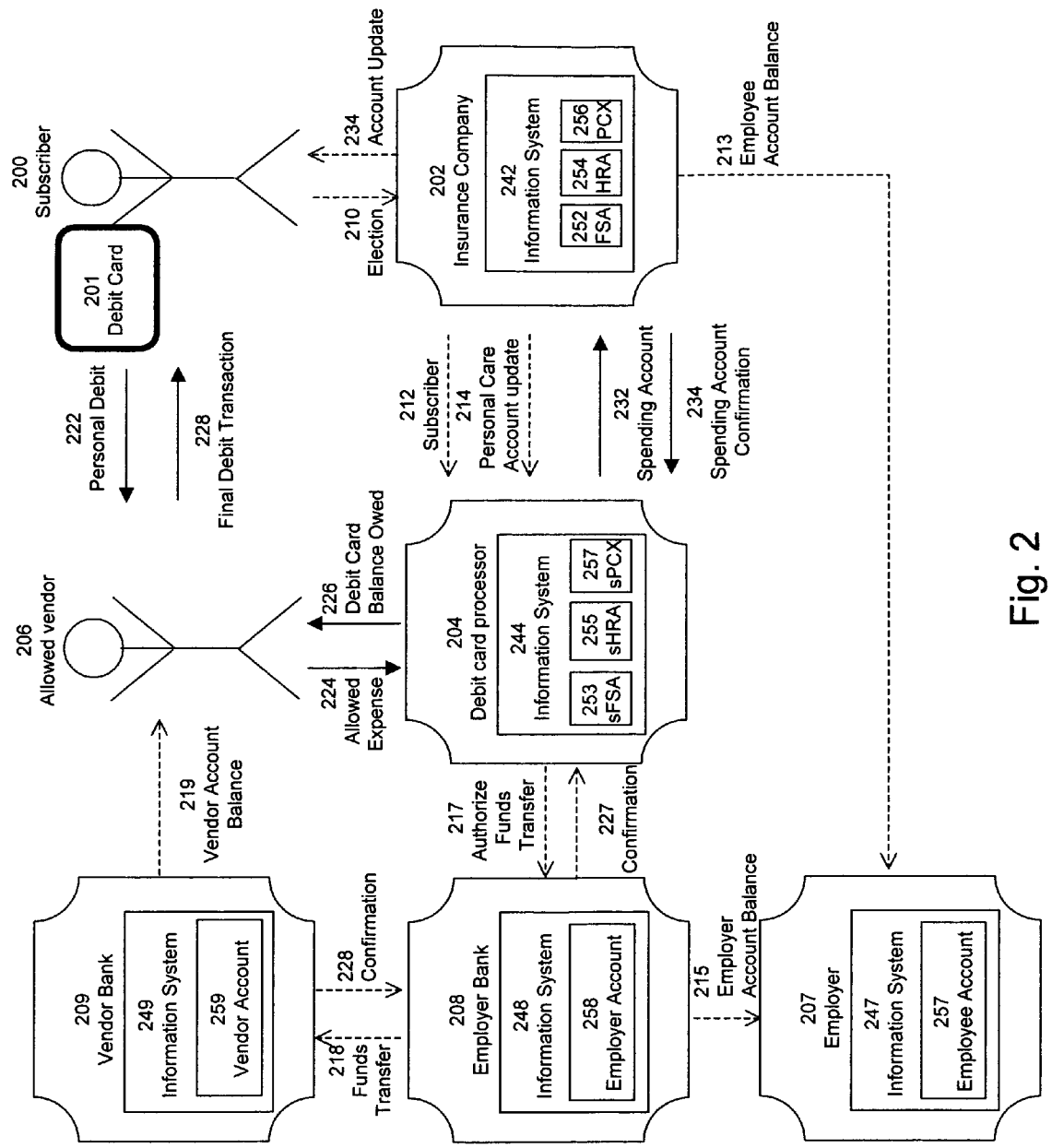
FIG. 2 is a diagram of the flow of information that occurs when a subscriber purchases an allowed expense.

All information transfers illustrated in FIGS. 1 and 2 may be by means of the modulation of an electronic or optical carrier wave transferred and/or relayed between one information system and another. For example, the transfer 112 of policy holder information between insurance company information system 142 and claims manager information system 144 may be over the Internet via information packets using a TCP/IP protocol. Said information packets cause the claims manager information system 144 to carryout certain desired steps of the invention, such as recording monetary credits in a client limit savings field 158, thus producing a concrete useful and tangible result.

The description of the insurance company, claims manager and other entities as separate entities in FIGS. 1 and 2 is, in part, for the convenience of explanation. Any number of entities illustrated in FIGS. 1 and 2 as being separate entities may exist as a single entity or may be subsets of each other. For example, claims manager 104 may be a department of insurance company 102.

Furthermore, entities illustrated as single entities may be aggregates of multiple entities. For example, a portion of the information system 142 of insurance company 102 may be under the control of an accounting firm, such as MHM Resources of Kansas City Mo., that provides information processing services to said insurance company.

The particular illustration of entities shown in FIGS. 1 and 2, however, has a surprisingly low unit cost per subscriber of carrying out the methods of the invention. Each entity can carryout its functions for multiple and even competing customers or clients. For example, claims manager 104 can carry out its functions for multiple competing insurance companies (who have a license to the invention) using the same information system 144. Thus the claims manager can take advantage of economies of scale and lower the unit cost of providing the concrete tangible results of the invention to multiple subscribers.

Initiating a Personal Care Account

Referring back to FIG. 1, a personal care account 152 is set up for a subscriber when the subscriber acquires an insurance policy offered by an insurance company 102.

Said insurance policy provides for the payment of an allowance for a given covered expense. If the cost of a given covered expense exceeds the allowance, then the subscriber must pay the difference. A per script maximum may be applied to provide additional financial protection for the subscriber. An annual "out of pocket" maximum may be included to provide the subscriber with additional financial protection. If the cost of a given covered expense is less than the allowance, then the subscriber is given a monetary credit for at least some of the unused portion of the allowance. Said credit may then be used to pay for certain allowed expenses. Said allowed expenses may or may not be the same as said covered expenses.

Said credits may be accumulated in a personal care account assigned to the subscriber.

After the subscriber acquires said insurance policy, election information 110 is transferred to the insurance company from the subscriber. The election information comprises personal identification of the subscriber and identification of the particular policy that the subscriber has elected to purchase.

The election information may be transferred to the insurance company in writing or via inputting said information into a web interface or other electronic means.

The insurance company then sets up a personal care account for the subscriber within their information system.

The personal care account comprises an identifier of the subscriber 155, and the balance 157 of the account. The personal care account data for a large number (e.g. more than 1000) of subscribers may be stored in an electronic data warehouse.

The balance of the personal care account assigned to a given subscriber may be set to zero when the subscriber first purchases the insurance policy. If the subscriber has purchased a renewal of an existing policy that had provided a personal care account, then the balance of said personal care account may be set to the balance remaining from the prior plan year. This is referred to as a year-to-year carryover of benefits.

The insurance policy may be a health insurance policy offered by an employer to its employees. The employees may only be allowed to purchase a policy during an "open enrollment period" or upon the occurrence of a qualifying "life event" (e.g. divorce, marriage, birth of child, etc.). The open enrollment period may last between one week and one month. The open enrollment period may be offered on an annual basis.

The health insurance policy may have a term of one year. The term may be referred to as a "plan year". The plan year may commence at some time after the conclusion of the open enrollment period.

At the end of an open enrollment period and prior to the commencement of a plan year, the insurance company may transfer policyholder information 112 regarding the subscriber to a claims manager 104. A claims manager is an entity that processes claims made by a subscriber against their insurance policy. A suitable claims manager for claims against the pharmacy benefits plan of a health insurance policy is Argus Health Systems, Inc. of Kansas City, Mo.

The policyholder information may comprise personal identifiers of the subscribers, and the identifiers of the insurance policies that the subscribers have purchased. The policyholder information may be encrypted and otherwise secured such that said transfer meets the necessary requirements for subscriber confidentiality, such as the requirements of HIPAA (US Health Insurance Portability and Accountability Act of 1996, incorporated herein by reference).

The policyholder information may also comprise pricing data for different covered expenses. For example, if the covered vendor is a pharmacist, the pricing data may comprise the prices for different prescriptions that the insurance company has previously negotiated with said pharmacist.

The information may be transferred in a mainframe data set over the Internet or by other suitable electronic means.

Subscriber ID Card

Once a subscriber has coverage under an insurance policy, they may be issued a personal ID card 108. The personal ID card may comprise the name of the subscriber and an identification number.

Different States within the United States may require certain information to be displayed on a personal ID card. Texas, for example, requires that the names of the dependents of a subscriber be displayed on a personal ID card if the insurance policy is a health insurance policy regulated by the Texas Insurance Commission.

Purchasing a Covered Expense

When a subscriber purchases a covered expense from a covered vendor 106, the subscriber provides coverage information 122 to the covered vendor. The coverage information may comprise a personal identifier for the subscriber.

The subscriber may transfer the information verbally or by other suitable means.

The covered vendor then transfers covered expense information 124 to the claims manager. The covered expense information may comprise a personal identifier of the subscriber and a product code for the covered expense.

The covered expense may be a prescription. The covered vendor may be a pharmacy, such as CVS Corporation of Woonsocket, R.I.

The covered expense information may be transferred via a modem connection or other electronic means.

After the claims manager receives the covered expense information, it sets up a covered expense record 154 in its information system 144. The covered expense record comprises data fields related to the covered expense purchase including a personal identifier 156 of the subscriber and a client limit savings field 158.

The client limit savings field is used to record any monetary credit that the subscriber may be entitled to as a consequence of the purchase of the covered expense. If the purchase price of the covered expense is less than the allowance for said covered expense, then the client limit savings field is set to at least a portion of the difference. If the purchase price of the covered expense is greater than or equal to the allowance then the client limit savings field is set to zero. The purchase price may include a sales tax on the purchase.

After the covered expense record is set up, the claims manager then looks up the actual allowance and price for the covered expense. The allowance is determined from the terms of the insurance policy that the subscriber purchased and the product code for the covered expense. The terms of the policy that the subscriber purchased are determined using the personal identifier of the subscriber and a database of terms for different policies. The database of terms for different policies may be part of the information system of the claims manager.

The claims manager may then set the value of the client limit savings field equal to at least a portion of the positive difference between the allowance and purchase price. Otherwise, the value is set to zero.

The value of the client limit savings field may be set to a negative number in certain circumstances. For example, if the subscriber is returning a covered expense from a previous purchase, then the client limit savings field would be set to the negative difference between the allowance and the price of the covered expense. This would cancel out the positive monetary credit accumulated by the subscriber when he/she originally purchased the covered expense.

The claims manager then transfers balance owed information 126 to the covered vendor. The balance owed information comprises the positive difference, if any, between the price of the covered expense and the allowance.

A prescription of Cephalexin, for example, might have a price of $36.89. The allowance for Cephalexin might be $40. The claims manager would record $3.11 in monetary credits in the client limit savings field. The claims manager would indicate to the covered vendor in the balanced owed information that the balance owed was $0.

In another example, a prescription of Flonase might have a price of $44.85. The allowance for Flonase might be $20. The claims manager would not record any monetary credits in the client limit savings field. The claims manager would indicate to the covered vendor in the balanced owed information that the balance owed is $24.85.

The balance owed information 126 may be transferred by modem or other electronic means.

After receiving the balance owed information, the covered vendor would then convey final transaction information 128 to the subscriber. The final transaction information might comprise the balance owed.

The final transaction information may be transmitted verbally or by other suitable means.

The subscriber and the covered vendor may then conclude the transaction of the purchase of the covered expense.

The covered vendor may be an automation, such as a vending machine, web page or an automated telephone system. Coverage information 122 and final transaction information 128 may be transmitted over the Internet or a phone system.

The subscriber may have an agent act on their behalf. The agent may be an automation, such as a computer implemented ordering system.

The subscriber may be a corporate entity, such as a health maintenance organization.

Updating the Personal Care Account

The personal care account 152 maintained by the insurance company may be updated by the claims manager on a periodic basis. The claims manager transmits accumulation amount information 132 to the insurance company on a periodic basis. The information may be transferred quarterly (i.e. every three months), monthly or more frequently. The information may be transferred in a flat file.

The accumulation amount information comprises a personal identifier of the subscriber and the sum of the monetary credits recorded in the client limit savings fields 158 contained in the covered expense records 154 associated with the subscriber. Said covered expense records are those that have been created since the prior transfer of accumulation amount information. The insurance company adds said monetary credits to the balance 157 in the personal care account 152 of the subscriber.

Monetary credits can be thought of as special purpose, private issue money. Thus the known systems and methods for securely electronically transmitting government issued money can be used for transmitting monetary credits.

The accumulation amount information may be entered into the information system of the insurance company by persons typing the information into a workstation. Said information may also be entered by direct file transfer.

The insurance company then transmits personal care account update information 134 to the subscriber. Personal care account update information may comprise the current balance in the subscriber's personal care account along with any changes and an indication of a reason for each change.

The personal care account update information may be transmitted via email. It may also be available on a personalized web site accessible to a given subscriber. The information may also be available via an automated phone system. The information may also be printed on paper and mailed.

The above described information transfers of election information 110, policy holder information 112, accumulation amount information 132, and account information 134 may be done in a batch mode for a large number of subscribers. Thus the cost of transferring, processing and storing said information can be kept low on a per subscriber basis.

Information Flow when Purchasing an Allowed Expense

FIG. 2 illustrates the flow of information of an exemplary embodiment of the present invention when a subscriber purchases an allowed expense. The figure shows subscriber 200, insurance company 202, debit card processor 204, allowed vendor 206, employer 207, employer bank 208 and vendor bank 209. The subscriber is an employee of the employer. The subscriber may have a debit card 201.

The subscriber and allowed vendor are shown as stick figures. Subscribers may comprise information systems, such as personal computers, with access to the Internet. Vendors may also comprise information systems, such as credit card processing terminals.

The other entities are shown as rectangles with recurved corners.

The debit card processor, insurance company, employer, employer bank and vendor bank comprise information systems 242, 244, 247, 248 and 249 respectively. They may also comprise their respective employees (not shown).

The information systems may comprise computers, software and communication devices.

Exemplary Embodiment

In the exemplary embodiment illustrated in FIG. 2, a personal care account 256 (PCX) for a subscriber is set up and administered as a modified version of a traditional "Health Reimbursement Arrangement" as defined in Internal Revenue Bulletin, No. 2002-28, Jul. 15, 2002, published by the US Internal Revenue Service. Said Bulletin is incorporated herein by reference.

Other traditional tax-advantaged accounts, as allowed by US law or comparable laws in other jurisdictions, may also be modified to serve as personal care accounts. These other traditional tax-advantaged accounts include Health Savings Accounts and Flexible Spending Accounts.

Traditional HRA

In a traditional Health Reimbursement Arrangement, an employer offers health care benefits to an employee. Said health care benefits are administered by an insurance company. As part of said health care benefits, said employer instructs said insurance company to set up a traditional HRA account 254 on behalf of an employee and provides an initial credit in said account. Said credit is to be used to help pay for said employee's health expenses. Said initial credit is referred to as an election amount.

During the course of a given plan year, the employee may purchase certain health related goods and services from an allowed vendor. If there is enough credit in the employee's HRA account, the insurance company will instruct the employer to pay the vendor directly for said goods and services. The employee never touches the money. The insurance company then records the cost of said goods and services as a debit to said employee's HRA account.

Because the employer pays the vendor directly and because the goods and services are allowable health care expenses as specified in section 213 of the US Internal Revenue Code (incorporated herein by reference), the funds used to pay for said allowable expenses are not treated as gross income to the employee and therefore are not taxed by the US federal government as gross income to the employee. Other restrictions apply. Hence the employee can receive more health care goods and services for a given election amount than if said election amount was provided directly by the employer to the employee as gross income.

Traditional HRA accounts allow for the rollover of unused funds from one year to the next. Hence if an employee does not use the entire election amount in a given year, the balance can be carried over to the next year and added to said employee's election amount for the subsequent year.

Traditional HRA accounts for large numbers of employees are administered by computer systems running traditional HRA account management software, such as winflexone® provided by MHM Resources Inc., of Kansas City Nebr.

It has been discovered that if the computer systems and software administering traditional HRA accounts are modified such that election amounts of HRA accounts can be updated on a more frequent basis than annually, then said systems can be used to administer the personal care accounts of the present invention while at the same time avoiding adverse tax consequences for employees. This is a surprisingly low cost means of implementing and administering personal care accounts.

Personal Care Accounts Administered as Modified HRA Accounts

Figure 3:
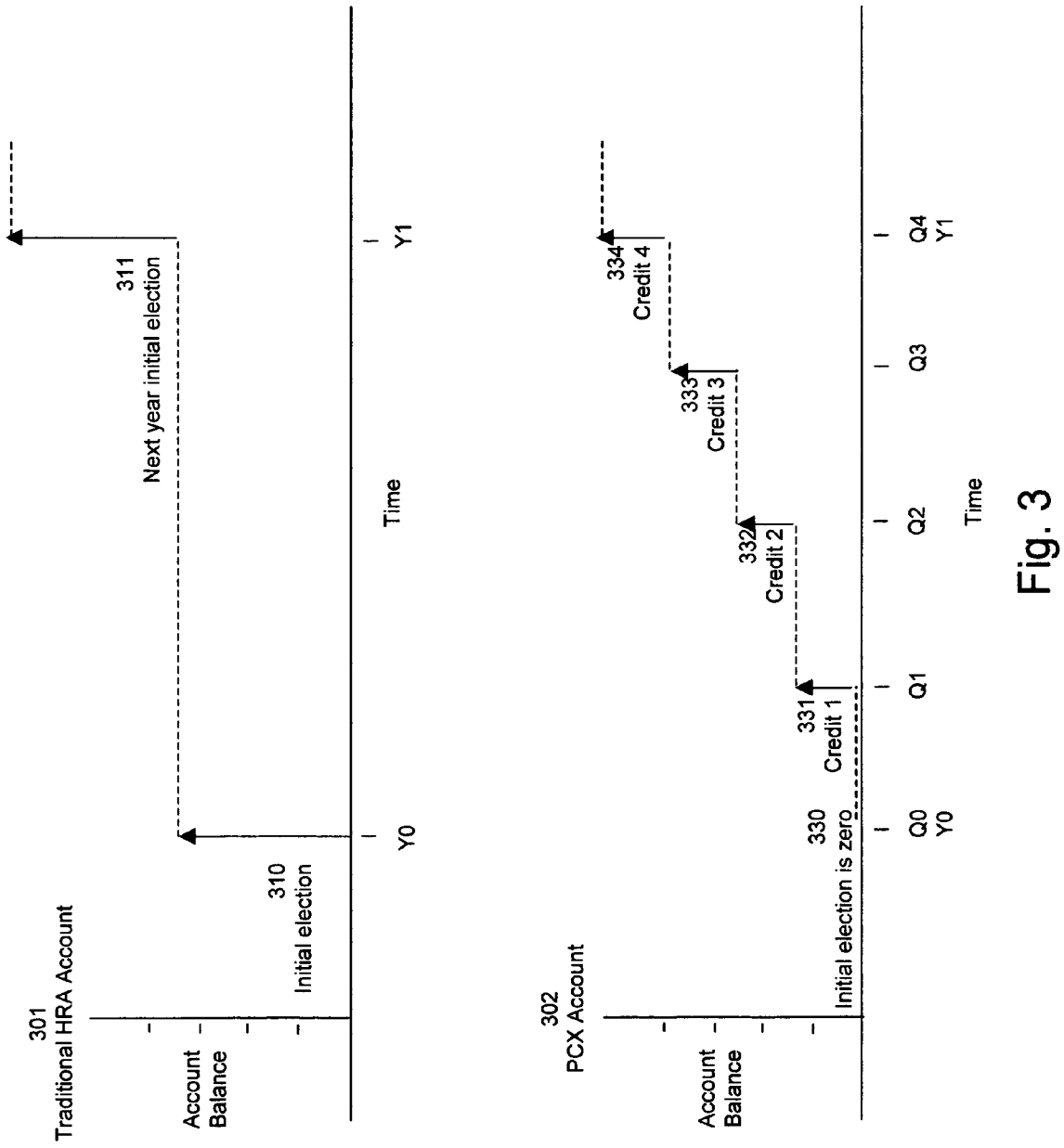
FIG. 3 shows two graphs illustrating how funds are credited to a traditional HRA account an HRA account that has been modified to serve as a personal care account (i.e. PCX account).

FIG. 3 illustrates how traditional HRA accounts can be modified to serve as personal care accounts.

Referring to FIG. 3, graph 301 illustrates how an election amount 310 for a traditional HRA account is set at the beginning, Y0, of a given plan year. Account balance is shown vertically. Time is shown horizontally. Additions to an account are shown as vertical arrows.

If the initial election amount for a particular employee is zero (and if there is no carryover from the prior year), then no HRA account is set up for that employee.

If there are no charges against the HRA account in said given plan year, then the account balance of the initial election amount 310 carries over into the next plan year Y1, and the next year's initial election amount 311 is added to the account.

Referring to graph 302, in order to implement a PCX account, the traditional HRA administration software and databases are modified such that:
  All subscribers who elect to have insurance plans providing accumulation of credits for unused portions of a given allowance for a pharmacy purchase are assigned a PCX account, even if the initial election amount is zero;
  Initial election amounts 330 of PCX accounts may be zero without causing the account to be deleted;
  Accumulated credits 331, 332, 333, 334, from given time periods (e.g. Q1) are treated as election amounts for the next given time period (e.g. Q2)
  Any balance of a PCX account unused as of the end of a given period of time is treated as a carryover to the next period of time.

Preferably, the frequency of credit updates to a PCX account is chosen such that the subscriber will perceive a direct feedback between their pharmacy choices and the accumulation of credits to be applied towards the purchase of allowed health care expenses. The longest said period should be is quarterly (i.e. every three months). If periods are longer, subscribers will be less likely to appreciate the impact of their decisions and the effectiveness of providing monetary credits to encourage cost saving behavior in subscribers will be reduced.

Shorter update periods such as monthly, weekly, daily or even real time are preferred unless they are so frequent that subscribers rarely see any credit to their PCX accounts. Subscribers might then ignore the credits and again, the effectiveness of providing monetary credits to encourage cost saving behavior in subscribers will be reduced.

Preferably, update frequency should be chosen such that subscribers see credits of a few dollars to a few hundred dollars on a regular basis. Update periods between weekly and quarterly will accomplish this.

Initiating a Personal Care Account

Referring back to FIG. 2 unless otherwise indicated, a personal care account 256 is set up for a subscriber as a modified traditional HRA account when the subscriber acquires an insurance policy offered by an insurance company 202. At that time, election information 210 is transferred to the insurance company from the subscriber. The insurance company then sets up a personal care account 256 (PCX) for the subscriber within their information system.

As used herein, insurance company 202 may also be a third party administrator, such as SHPS of Louisville Ky. A third party administrator is an entity that administers one or more traditional HRA, FSA or HSA accounts on behalf of the subscribers of one or more health insurance companies or other entities.

The balance of a personal care account may be set to zero when a subscriber first purchases the insurance policy. If the subscriber has purchased a renewal of an existing policy, then the balance of the personal care account may be set to the balance of the personal care account remaining from the prior plan year.

The insurance policy may be a health insurance policy offered by an employer to its employees. The employees may be allowed to purchase a policy during an open enrollment period. They also may be allowed to purchase a policy if they experience a qualifying life event, such as joining the company in the middle of a plan year.

At the end of an open enrollment period and prior to the commencement of a plan year, the insurance company may transfer subscriber information 212 regarding all of the subscribers in a given employer group to a debit card processor 204. A suitable debit card processor for the pharmacy benefits plan of a health insurance policy is Metavante of Milwaukee Wis.

Said subscriber information may comprise personal identifiers of the subscribers, and the balance of the subscribers' respective personal care accounts 256.

Subscriber information may also contain identifier codes of allowed vendors.

The information may be transferred in a flat file over the Internet or by other suitable electronic means.

Said debit card processor then sets up stand-in personal care accounts 257 (sPCX) for the subscribers within its own information system 244.

The insurance company may also transmit personal care account update information 214 to the debit card processor from time to time. Personal care account update information may comprise personal identifiers of subscribers and additional monetary credits (e.g. items 331, 332, 333, 334 of FIG. 3) to the subscribers' respective personal care accounts. Said monetary credits may have been received (132 FIG. 1) by said insurance company (102 FIG. 1, 202 FIG. 2) from a claims manager (104, FIG. 1).

Said debit card processor will then update their sPCX accounts 257.

There may be negative adjustments to a given sPCX account 257, such as if a subscriber leaves the employ of their employer 207. In that case, the sPCX account may be closed out and the subscriber's monetary credits will be forfeited.

Other Spending Accounts

The subscriber information 212 or the personal care account update information 214 may further comprise balance and update information regarding other types of spending accounts that may be assigned to each subscriber.

Certain subscribers, for example, may each have a flexible spending account 252. In the United States as of Jun. 1, 2004, flexible spending accounts are governed by Section 213(a) of the Internal Revenue Code, which is incorporated herein by reference. This Section allows subscribers to contribute a certain fraction of their income to flexible spending accounts on a pretax basis. The contributions to a flexible spending account can be used to purchase certain 213(a) allowable expenses, such as health care costs. Contributions to flexible spending accounts must be used for 213(a) allowable expenses in a given tax year or within two and one half months thereafter, or they will be forfeited.

"Allowed expenses" as used herein may be a subset of the 213 (a) allowable expenses, such as health care costs, as defined by Section 213(a) of the Internal Revenue Code or other comparable regulations in force at different times or in different jurisdictions.

One or more subscribers may also have traditional HRA accounts 254 assigned to them. Said conventional HRA accounts would be set up at the beginning of a plan year with a given election amount as described above.

The debit card processor will set up and update stand-in spending accounts 253, 255, 257 assigned to each subscriber for the flexible spending accounts, traditional HRA accounts, personal care accounts, and other accounts indicated by the insurance company. The balances of these accounts will be used to pay for allowed expenses.

In the event that a subscriber makes a purchase of an allowed expense, certain spending accounts assigned to said subscriber may be debited before other accounts. For example, a flexible spending account may be debited before a personal care account due to the fact that the balance in a flexible spending account is forfeited at the end of a tax year whereas the balance in a personal care account may be rolled over from one plan year to the next.

Subscriber Debit Card

Once a subscriber has coverage under an insurance policy, they may be issued a debit card 201. The debit card may be made from plastic. The debit card may comprise raised letters indicating the subscriber's name and debit card number. The card may further comprise a magnetic strip, electronic chip, or other suitable means into which has been encoded subscriber identification information. The card may further comprise an area that the subscriber may sign.

Alternatively, subscribers that only have PCX accounts an no other FSA or conventional HRA accounts may only be issued debit cards when the balance of their personal care accounts exceeds a certain threshold, such as $10.

Purchasing an Allowed Expense

When a subscriber purchases an allowed expense from an allowed vendor 206, the subscriber provides personal debit information 222 to the allowed vendor. The personal debit information may comprise a personal identifier for the subscriber and a debit card number.

The subscriber may transfer the information to the vendor by providing their debit card to the allowed vendor and the allowed vendor may then swipe the debit card in a debit card reader.

The allowed vendor then transfers allowed expense information 224 to the debit card processor. The allowed expense information may comprise a personal identifier of the subscriber, debit card number, the price for the allowed expense and a merchant identifier code assigned to the allowed vendor.

The merchant identifier code may indicate the type of products or services that the allowed vendor sells. This can be used by the debit card processor to determine, at least in part, if the allowed expense is indeed allowed. In this example, allowed means that it conforms to IRS regulations for allowed health care expenses as described above.

The allowed expense may be the cost of a prescription. The allowed vendor may be a pharmacist, such as CVS Corporation.

The allowed expense may alternatively be the copayment due for a doctor's visit.

The allowed expense information may be transferred via a modem connection or other suitable means.

After the debit card processor receives the allowed expense information, it checks to see if the expense is indeed allowable. As indicated above, a suitable means to determine, at least in part, if an expense is allowable is to compare the merchant identifier code with a list of allowed merchant identifier codes.

If the expense is indeed allowable, the debit card processor then examines the stand-in spending accounts 253, 255 and 257 assigned to said subscriber to determine if the collective balance in these accounts is sufficient to cover the cost of the expense. If it is, then the debit card processor debits the appropriate spending account(s) by the cost of the allowed expense. If it is not, then the debit card processor debits the spending accounts by what they have available and records the balance of what is owed.

The debit card processor then transfers debit card balanced owed information 226 to the allowed vendor. The debit card balance owed information comprises the positive difference between the price of the allowed expense and the collective balance of the spending accounts assigned to the subscriber.

For example, an allowed expense might include the cost of a pair of glasses. The glasses might cost $300. A subscriber might have $200 in their stand-in flexible spending account 253 and $150 in their stand-in personal care account 257. The debit card processor would first debit the stand-in flexible spending account by $200 and then debit the stand-in personal care account by $100. The balance of the stand-in flexible spending account would be zero. The balance of the stand-in personal care account would be $50. The debit card balance owed information would indicate that the subscriber did not owe any money for the glasses.

Alternatively, for the same glasses, a subscriber might have $100 in their stand-in flexible spending account and $50 in their stand-in personal care account. The debit card processor would first debit the stand-in flexible spending account by $100 and then debit the stand-in personal care account by $50. The balance of both spending accounts would be zero. The debit card balance owed information would indicate that the subscriber owed the allowed vendor $150 for the glasses.

After receiving the balance owed information, the allowed vendor would then convey final debit transaction information 228 to the subscriber. The final debit transaction information might comprise the balance owed.

The final debit transaction information may be transmitted verbally.

The subscriber and the allowed vendor may then conclude the transaction of the purchase of the allowed expense.

The allowed vendor may be an automation, such as a web page, automated telephone system or vending machine dispensing prescription drugs. Personal debit information 222 and final debit transaction information 228 may be transmitted over the Internet, phone system or other telecommunications means.

The subscriber may have an agent act on their behalf. The agent may be an automation, such as a computer implemented ordering system.

The subscriber may be a corporate entity, such as an HMO.

Transferring Monetary Credits from an Insurance Company to a Debit Card Processor The personal care accounts 256 and other accounts 252, 254, assigned to a subscriber and maintained by the insurance company may be updated by the debit card processor on a real time basis when a covered expense is purchased. When a purchase takes place, the debit card processor transmits spending account information 232 to the insurance company.

The spending account information comprises a personal identifier of the subscriber and the debits or credits to their spending accounts. The insurance company subtracts the debits or adds the credits to the respective balances of the personal care accounts and other accounts assigned to the subscriber.

The spending account information may be entered into the insurance company's information system automatically.

The transmission of a PCX debit from the debit card processor to the insurance company can be considered to be a transfer of PCX monetary credits from the insurance company to the debit card processor. Thus the systems and methods for electronically transferring government issued cash from one entity to another would be suitable for transferring Personal Care Account update information from the debit card processor to the insurance company. Said transfer, therefore, may comprise a transmission of a spending account confirmation 234 from the insurance company to the debit card processor confirming that the PCX monetary credits are indeed available for said subscriber.

If the transfer of spending account information 232 and spending account confirmation information 234 is not completed in a timely manner, such as, for example, due to unscheduled downtime in the communications link carrying said information, then said debit card manager 204 may make provisional adjustments to the appropriate stand-in accounts 253, 255, 257 and still transfer debit card balance owed information 226 to said allowed vendor on a real time basis. Said provisional adjustments are later confirmed when the spending account confirmation 234 is subsequently received.

Updating a Subscriber and Employer

The insurance company may periodically transmit account update information 234 to a subscriber. Account update information may comprise the current balance in the subscriber's personal care account along with any changes to the account and an indication of a reason for each change. Said information may be transmitted quarterly.

The insurance company may also periodically transmit employee account balance information 213 to a given employer 207 on a periodic basis. Employee account balance information may comprise balances, credits and debits to the traditional HRA and PCX accounts associated with the subscribers who are employees of said employer. The employer may update an employee account database 257 based on said employee account balance information.

Actual Payment of Allowed Expenses

Paying a vendor for allowed expenses debited to a subscriber's employer sponsored stand-in PCX account 257 may be done in the same manner as is traditionally done for a traditional stand-in HRA account.

On a periodic basis, such as daily, the debit car processor transmits an authorization for funds transfer 217 to the employer's bank 208. Said authorization of funds transfer information may comprise an identification of the employer's bank, an identification of the employer's account held by said bank, and identification of the vendor's bank, and identification of the vendor's account held by the vendor's bank, and an amount of government issued cash or other financial instrument that is to be transferred from the employer to the vendor.

The employer's bank then transfers 218 funds from the employer's bank account 258 to the vendor's bank 209. The vendor's bank then credits the funds transfer to the vendor's bank account 259. Appropriate confirmation information 228, 227 is relayed back to the employer's bank and debit card processor.

Thus government issued funds to satisfy debits to a subscriber's PCX account are provided directly from an employer to a vendor.

The employer's bank will then provide account balance information 215 to the employer showing debits to their account 258. The vendor's bank will similarly provide vendor account balance information 219 to the allowed vendor showing credits to their account 259.

Substantiation of Allowed Expenses

It may be necessary to substantiate allowed expenses to confirm that they are indeed allowed. For example, if the allowed expenses are allowable expenses under Section 213 (a) of the Internal Revenue Service Code, then it is a legal requirement in the United States that the allowed expenses be substantiated.

Suitable methods for substantiation are described in Rev. Rul. 200343, 2003-21 I.R.B. 935 by Barbara Pie, published May 16, 2003, available at www.irs.gov/pub/irs-drop/rr-0343.pdf (last viewed Jul. 29, 2004), and incorporated herein by reference.

Example

An insurance company offered a new pharmacy benefits plan comprising allowances for drugs in a given group of drugs. Said new pharmacy benefits plan was offered as an alternative to a conventional pharmacy benefits plan requiring copayments for drugs in a given tier of drugs. Both plans were offered to the United States employees of a publicly traded corporation (the employer). Drugs in the new pharmacy benefits plan were assigned into 4 different Groups according to their anticipated impact on subsequent covered medical costs. 18% of said employees selected the new plan in the first year it was offered. These employees thus became subscribers to the new pharmacy benefits plan.

It was subsequently discovered that the employees of said corporation wished that they could accumulate the unused portions of their allowances so that said unused portions could be applied to other allowed out-of-pocket medical expenses. Hence in the second year that the new pharmacy benefits plan was offered, provision was made to allow employees to accumulate unused portions of their allowances and apply said unused portions to other allowed out-of-pocket medical expenses as specified in the policy. Surprisingly, 40% of the employees now became subscribers to the new pharmacy benefits plan.

Said provision for accumulating unused portions of said allowances comprised creating personal care accounts for all employees selecting the new plan. The personal care accounts were administered as modified Health Reimbursement Arrangements. The personal care accounts were administered using Health Reimbursement Arrangement software that had been modified to allow for an initial account balance of zero and the subsequent accumulation of monetary credits throughout a given plan year. Said monetary credits could also be carried over from one plan year to the next plan year.

Each of said subscribers was provided with a health plan identification (ID) card. Whenever a subscriber purchased a prescription drug, the pharmacy benefits manager adjudicating said purchase set a client limit savings field contained in a covered expense record associated with said purchase to the positive difference between the allowance for said drug and the cost of said drug.

The pharmacy benefits manager would then transmit the accumulated monetary credits associated with each subscriber to said insurance company on a quarterly basis. The insurance company would then update the personal care accounts associated with each subscriber. The insurance company would then provide each subscriber with an update of their personal care accounts indicating the accumulation of said credits. The insurance company also made the personal care account information for each subscriber available on the Internet. Each subscriber had to provide appropriate security information, such as a user ID and password, to view their account balance.

The insurance company would provide a debit card to a subscriber when their personal care account balance exceeded $10 for the first time.

When a subscriber purchased an allowed health care expense, such as a prescription drug or doctor copayment, they would present their debit card to the vendor. The vendor would then submit a request for payment to a debit card processor. The debit card processor would then check to see if there were enough credits in the subscriber's personal care account to cover at least a portion of the allowed health care expense. If there were enough credits, then the debit card manager would indicate to the vendor that no further balance was owed. The debit card vendor would then direct the employer's bank to debit the employer's bank account, transfer funds to the vendor's bank and instruct the vendor's bank to credit the vendor's bank account with said funds. Thus the vendor would be paid directly by the employer and the subscriber would not have to declare said payment as income on their tax return.

The debit card manager would also indicate to the insurance company that there was a debit to the subscriber's personal care account.

All transactions were carried out with known security protocols sufficient to reduce the incidence of fraud or error to an appropriate level and to comply with all necessary governmental regulations concerning patient privacy.

The cost savings to subscribers exceeded expectations. 4,800 subscribers accumulated $174,000 worth of credits in their personal care accounts in 90 days. This indicates that subscribers were actively seeking lower cost but nonetheless effective drugs in order to accumulate credits.

Conclusion

One of skill in the art will recognize that insurance is a regulated industry. One practicing the methods described and claimed herein will want to maintain compliance with all applicable local, state and federal regulations, to ensure that the insurance policy is properly presented to the insured, premiums are properly approved, underwriting properly occurs, all necessary regulatory approvals are in place, etc.

While particular embodiments of the present invention have been illustrated and described, it would be obvious to those skilled in the art that various other changes and modifications can be made without departing from the spirit and scope of the invention. Any of the aspects of the present invention found to offer advantages over the state of the art may be used separately or in any suitable combination to achieve some or all of the benefits of the invention disclosed herein.

Therefore, we claim:

1. A computerized method for an insurance company to provide insurance coverage to a subscriber, said method comprising;
    a) storing in a database at a server insurance policy data, said insurance policy data comprising;
        i. data for a plurality of allowances to pay for covered products or services, wherein each allowance for a covered product or service comprises to a maximum amount said insurance company pays for said covered product or service;
        ii. data of the accumulation of monetary credits in a personal care account assigned to said subscriber, said monetary credits being equal to the difference between the cost of said covered product or service and the allowance for said covered product or service;
        iii. a provision for said subscriber to cover the cost of at least a portion of an allowed expense using at least a portion of said accumulated monetary credits, said allowed expense specified in said insurance policy;
    b) accepting the payment of a premium for said insurance policy, said step of accepting said payment of said premium being necessary for said insurance policy to be in force;
    c) receiving at said server election information of said subscriber, said election information comprising personal identification data for said subscriber and said subscriber's election of said insurance policy;
    d) electronically transferring said election information to said insurance company;
    e) storing said election information of said subscriber in association with said personal care account within said electronic database;
    f) processing at a computer claim data for said covered product or service according to said insurance policy elected by said subscriber, said claim data comprising an actual cost for said covered product or service;
    g) accessing at said computer said database to locate an allowance for said covered product or service;
    h) calculating at said computer a monetary credit associated with said claim by calculating a difference between said allowance for said covered product or service and said actual cost for said covered expense; and i) if said difference is:
  i) positive, updating said database to increase by said monetary credit a balance in said personal care account for a subscriber; and
  ii) negative or zero, leaving said balance in said personal care account for a subscriber unchanged.

2. The computerized method of claim 1 wherein said insurance policy comprises a pharmacy benefits plan wherein said covered products or services are prescription drugs and said allowed expenses are medical costs of said subscriber.

3. The computerized method of claim 2 wherein said allowances are determined by the anticipated impact of a given prescription drug on the anticipated subsequent health care costs that said subscriber would experience if said subscriber did not take said prescription drug when prescribed.

4. The computerized method of claim 2 wherein said medical costs are those that qualify for payment by an employer without said payment resulting in taxable gross income being assigned to said subscriber.

5. The computerized method of claim 4 wherein said medical costs are those that qualify under a tax code.

6. The computerized method of claim 1 wherein said personal care account is a modified Heath Reimbursement Account (HRA) account wherein said HRA has been modified to allow for an initial balance of zero and to allow for one or more additional election amounts to be credited to it during the course of a given plan year.

7. The computerized method of claim 1 wherein said insurance company is an employer, said insurance coverage is self funded by said employer, said subscribers are the employees of said employer and wherein said employer pays an administrative fee to a licensed insurance company such that said licensed insurance company will administer said insurance policy on behalf of said employer.

8. The computerized method of claim 1, wherein said monetary credits are redeemed by said subscriber to cover at least a portion of the cost of one or more of said allowed expenses provided by one or more allowed vendors.

9. The computerized method of claim 1, further comprising the step of:
  processing at said computer a purchase for said allowed expense according to said insurance policy elected by said subscriber.

10. The computerized method of claim 9, further comprising the step of:
  accessing said database to determine whether said purchase is an allowed expense.

11. The computerized method of claim 10, further comprising the step of:
  crediting at least a portion of the cost of said purchase with said monetary credits of said subscriber if said purchase is an allowed expense provided by one or more allowed vendors.

12. The computerized method of claim 11, further comprising the step of:
  if said purchase cost exceeds said monetary credits in said subscriber's personal care account, requesting from said subscriber a payment of the difference between the amount of said monetary credits in said personal care account and said purchase cost.

13. The computerized method of claim 12, further comprising the step of:
  updating said personal care account in said electronic database with said monetary credit credited for said purchase.

14. The computerized method of claim 1, further comprising the step of:
  if said actual cost exceeds said allowance for a covered expense, requesting from said subscriber a payment of the difference.

* * * * *